(12) United States Patent
Wuppuluru

(10) Patent No.: US 11,040,129 B2
(45) Date of Patent: Jun. 22, 2021

(54) MOBILE CONTINUOUS AMBULATORY PERITONEAL DIALYSIS SYSTEM

(71) Applicant: Gowrishankar Wuppuluru, Chennai (IN)

(72) Inventor: Gowrishankar Wuppuluru, Chennai (IN)

(*) Notice: Subject to any disclaimer, the term of this patent is extended or adjusted under 35 U.S.C. 154(b) by 781 days.

(21) Appl. No.: 16/091,971

(22) PCT Filed: May 15, 2015

(86) PCT No.: PCT/IN2015/000206
§ 371 (c)(1),
(2) Date: Oct. 5, 2018

(87) PCT Pub. No.: WO2015/173833
PCT Pub. Date: Nov. 19, 2015

(65) Prior Publication Data
US 2019/0224400 A1    Jul. 25, 2019

(30) Foreign Application Priority Data

May 13, 2014  (IN) .............................. 687/CHE/2014

(51) Int. Cl.
*A61M 1/28* (2006.01)
*A61M 1/26* (2006.01)

(52) U.S. Cl.
CPC .............. *A61M 1/284* (2014.02); *A61M 1/28* (2013.01); *A61M 1/262* (2014.02); *A61M 1/267* (2014.02);
(Continued)

(58) Field of Classification Search
CPC ........ A61M 1/284; A61M 1/28; A61M 1/282; A61M 1/267; A61M 1/262; A61M 1/14;
(Continued)

(56) References Cited

U.S. PATENT DOCUMENTS 5,290,222 A * 3/1994 Feng ..................... A61M 39/04
604/174
5,350,357 A    9/1994 Kamen et al.
(Continued)

FOREIGN PATENT DOCUMENTS

WO    2008082528 A1    7/2008
WO    2009157878 A1    12/2009

OTHER PUBLICATIONS

International Search Report for PCT/IN2015/000206 dated Oct. 7, 2015.
(Continued)

*Primary Examiner* — Nathan R Price
*Assistant Examiner* — Tasnim Mehjabin Ahmed
(74) *Attorney, Agent, or Firm* — Ladas & Parry, LLP

(57) ABSTRACT

A wearable mobile continuous ambulatory peritoneal dialysis (mCAPD) system, includes an mCAPD module mounted on a front portion of a wearable belt, wherein the mCAPD module comprises a micro-peristaltic pump disposed in a corresponding front portion, and an electronic control board connected to the micro-peristaltic pump for controlling and managing the mCAPD process, a fluid bag containing a dialysate fluid, attached to the wearable belt and to the electronic control board, and a sterile connector having a tube portion fixed into a guide section of the micro-peristaltic pump, and a first connecting end for connecting to a first tube inserted into a peritoneum cavity of the human body, and a second connecting end for connecting to a second tube attached to the fluid bag. Upon rotation, the micro-peristaltic pump enables a flow of fluid between the peritoneum cavity and the fluid bag.

9 Claims, 5 Drawing Sheets

(52) U.S. Cl.
CPC ............... *A61M 2205/3368* (2013.01); *A61M 2205/3372* (2013.01); *A61M 2205/36* (2013.01); *A61M 2205/3653* (2013.01); *A61M 2209/088* (2013.01)

(58) Field of Classification Search
CPC ............ A61M 1/16; A61M 2205/3653; A61M 2205/3368; A61M 2205/36; A61M 2205/3372; A61M 2205/12; A61M 2205/121; A61M 2039/088; A61M 39/10; A61M 39/16
See application file for complete search history.

(56) References Cited

U.S. PATENT DOCUMENTS

| | | | |
|---|---|---|---|
| 5,873,853 A * | 2/1999 | Keilman | A61M 1/281 604/67 |
| 6,086,574 A * | 7/2000 | Carroll | C12M 99/00 604/533 |
| 6,168,578 B1 * | 1/2001 | Diamond | A61M 1/28 2/312 |
| 7,896,830 B2 | 3/2011 | Gura et al. | |
| 2010/0022937 A1 * | 1/2010 | Bedingfield | A61M 1/28 604/6.09 |
| 2010/0312174 A1 * | 12/2010 | Hoffman | A61M 1/28 604/29 |

OTHER PUBLICATIONS

Written Opinion of the International Search Authority PCT/IN2015/000206 dated Oct. 7, 2015.
International Preliminary Report on Patentability Chapter I PCT/IN2015/000206 dated Oct. 7, 2015.

* cited by examiner

MOBILE CONTINUOUS AMBULATORY PERITONEAL DIALYSIS SYSTEM

CROSS-REFERENCE TO RELATED APPLICATION

The present application is the U.S. national phase of PCT Application No. PCT/IN2015/000206 filed on May 15, 2015, which claims Priority to Indian Application 687/CHE12014 filed on May 13, 2014, the disclosures of which are incorporated herein by reference.

BACKGROUND

Field of the Invention

The present invention relates generally to peritoneal dialysis system, and more particularly to mobile continuous ambulatory peritoneal dialysis (MCAPD) system.

Description of the Related Art

Nowadays, more and more people including younger generation are being diagnosed with end stage renal failure (ESRF) due to hectic lifestyles and stress. The ESRF severely limits their lifestyles, occupation and opportunities, and the only option available to these patients for survival is kidney transplant. However, only a few hundreds of patients are lucky enough to have a transplant, and the others have to depend on regular dialysis for their survival. Presently, there are two major types of dialysis treatments available for the kidney patients, hemodialysis and the continuous ambulatory peritoneal dialysis (CAPD). The hemodialysis treatment requires sophisticated equipment, manpower and hospitals, and is currently available only to patients living in metros and tier II cities and towns.

In the CAPD system, a dialysate fluid is pumped into a peritoneal cavity of user through a tube inserted into the cavity, and is allowed to dwell in the cavity for about four hours. Due to the difference in concentration of the blood flowing and dialysate fluid on either sides of the peritoneum membrane, the impurities in blood like urea, creatinin etc., permeates into the dialysate fluid through the membrane, due to osmosis. The dialysate fluid is drained out after approximately four hours, and the whole process is repeated up to four times a day, depending on the patient's condition.

However, the patients have to go back to home or any sterile environment to carry out the dialysis using the CAPD system, which constitutes a typical fill procedure of about fifteen minutes, and the drain procedure of about twenty minutes with an additional time required for travel to reach their place of dialysis. Doing this up to four times at a fixed place undoubtedly interrupt the occupation and work schedule of the patients.

OBJECTS OF THE INVENTION

An object of the invention is to provide a dialysis system that offers total mobility to the patients during dialysis process, thereby unshackling their chains with beds and dialysis machines.

Another object of the invention is to provide an infection free dialysis process that can be carried out anywhere without compromising the safety, and effectiveness of the dialysis.

Yet another object of the invention is to provide a dialysis system that enables the patients to lead a normal lifestyle and continue their work and studies, unhindered by the disease.

Yet another object of the invention is to provide a dialysis system that enables the patients in remote and rural places who do not have the required hospitals and healthcare centers, to carry out the dialysis.

Yet another object of invention is to create an automatic patient monitoring system for dialysis patients to monitor and alert on their quality of dialysis everytime, and allow doctors and patients to take preventive measures and maintain the clinical condition of the patient in a better way.

SUMMARY OF THE INVENTION

Various embodiments of the present invention provide a wearable mobile continuous ambulatory peritoneal dialysis (mCAPD) system, that includes a mCAPD module mounted on a front portion of a wearable belt, wherein the mCAPD module comprises a micro-peristaltic pump disposed in a corresponding front portion, and an electronic control board connected to the micro-peristaltic pump for controlling and managing the mCAPD process; a fluid bag containing a dialysate fluid, attached to the wearable belt and to the electronic control board; and a sterile connector having: a tube portion fixed onto a guide section of the micro-peristaltic pump; a first connecting end for connecting to a first tube inserted into a peritoneum cavity of the human body; and a second connecting end for connecting to a second tube attached to the fluid bag, wherein upon rotation, the micro-peristaltic pump enables a flow of fluid between the peritoneum cavity and the fluid bag, through the tube portion of the sterile connector, and wherein a direction and speed of rotation of the micro-peristaltic pump is controlled by the electronic control board.

BRIEF DESCRIPTION OF THE DRAWINGS

The following detailed description of illustrative embodiments is better understood when read in conjunction with the appended drawings. For the purpose of illustrating the present disclosure, exemplary constructions of the disclosure are shown in the drawings. However, the invention is not limited to specific methods and instrumentalities disclosed herein. Moreover, those in the art will understand that the drawings are not to scale. Wherever possible, like elements have been indicated by identical numbers.

DETAILED DESCRIPTION OF THE EMBODIMENTS

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning as supplemented by the discussion immediately below. As used in the specification and claims, the singular forms "a", "an" and "the" include plural references unless the context clearly dictates otherwise.

Those with ordinary skill in the art will appreciate that the elements in the Figures are illustrated for simplicity and clarity and are not necessarily drawn to scale. There may be additional components described in the foregoing application that are not depicted on one of the described drawings. In the event such a component is described, but not depicted in a drawing, the absence of such a drawing should not be considered as an omission of such design from the specification.

Thus, the present invention has been described herein with reference to a particular embodiment for a particular application. Although selected embodiments have been illustrated and described in detail, it may be understood that various substitutions and alterations are possible. Those having ordinary skill in the art and access to the present teachings may recognize additional various substitutions and alterations are also possible without departing from the spirit and scope of the present invention.

Figure 1:
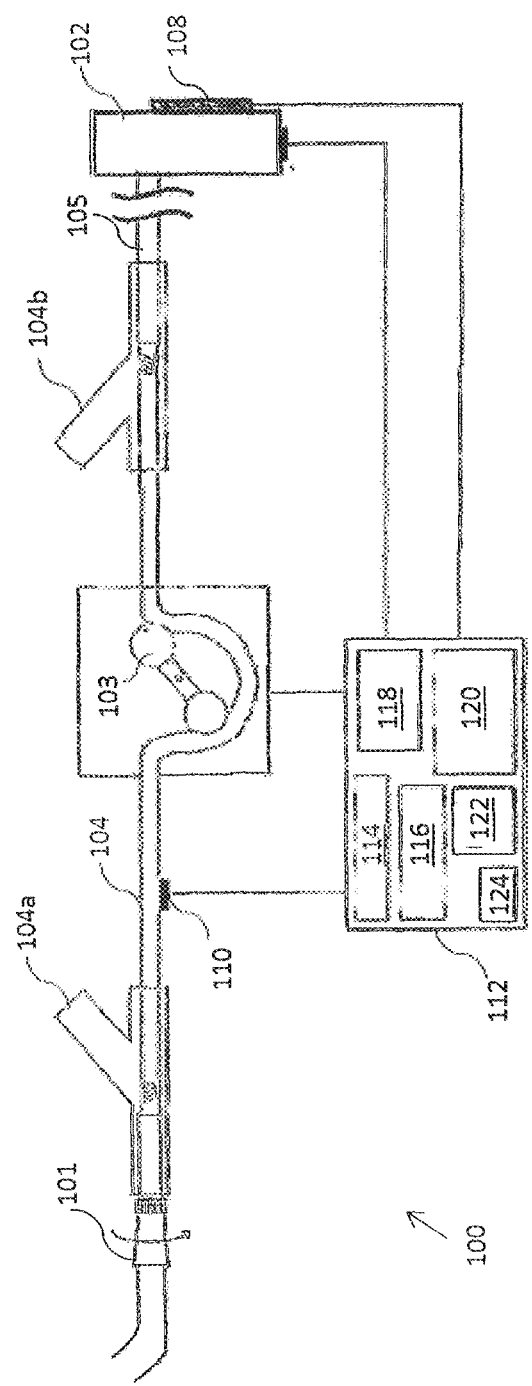
FIG. 1 is a schematic block diagram of a mobile continuous ambulatory peritoneal dialysis (mCAPD) system, in accordance with an embodiment of the present invention.

FIG. 1 is a schematic block diagram of a mobile CAPD (mCAPD) system 100, in accordance with an embodiment of the present invention. The mCAPD system 100 includes a first tube 101 inserted into a peritoneum cavity of the body, a fluid bag 102 for holding dialysate fluid, a micro-peristaltic pump 103, and a sterile connector 104 connecting the first tube 101 and the fluid bag 102 through the micro-peristaltic pump 103. The sterile connector 104 has a first receiving end 104a for connecting to the first tube 101, and a second receiving end 104b for connecting to a second tube 105 of the fluid bag 102.

The mCAPD system 100 further includes a heating element 108 attached to the fluid bag 102 for heating the dialysate fluid, a fluid flow sensor 110 attached to the sterile connector 104 for sensing the flow of dialysate fluid flowing there through, and an electronic control board 112 connected to the fluid flow sensor 110, fluid bag 102, the micro-peristaltic pump 103, and the heating element 108 for controlling and managing the mCAPD process. In an embodiment, the mobile CAPD (mCAPD) system 100 is configured to be worn by the user like a belt on their waist, in order to carry out the dialysis anytime and anywhere. The wearable aspect of the (mCAPD) system 100 is illustrated in detail with respect to FIG. 2

The sterile connector 104 provides a path for the dialysate fluid to flow into the patient's body from the fluid bag 102 through the first tube 101. The sterile connector 104 provides a safe infection free connection to be established between the first tube 101, and the fluid bag 102 even in unsterile environments, as the connection is made by holding the components through the sterile connector 104, and opening the critical components under the sterile connector 104 without exposing them to external environment at any stage. In an example, the sterile connector 104 is made sterile through standard sterility processes of ethylene oxide, and packaged in a sterile use only once package. This sterile connector is advised to be used once daily, and to be discarded after every dialysis cycle, to avoid any risk of infection. One dialysis cycle includes a fill process, followed by a drain process after an elapse of a predetermined period.

During the fill process, the fluid is allowed to flow from the fluid bag 102 towards the first tube 101, and during the drain process, the fluid is drained out from the first tube 101 to a drain bag (not shown).

The micro-peristaltic pump 103 controls flow of dialysate fluid between the patient's body and the fluid bag 102. The sterile connector 104 is made to pass through the guide of the micro-peristaltic pump 103. When the micro-peristaltic pump 103 rotates, the rollers of the micro-peristaltic pump 103 squeezes out the fluid flowing through the sterile connector 104. The micro-peristaltic pump 103 rotates in a clockwise/anticlockwise direction during the fill process to allow the fluid to flow from the fluid bag 102 towards the first tube 101, and rotates in an opposite direction during the drain process to allow fluid flow from the first tube 101 to the drain bag. In an embodiment, the direction and speed control of the micro-peristaltic pump 103 is managed by the electronic control board 112 which activates the micro-peristaltic pump 103 as per a predefined process set by the user.

The electronic control board 112 includes a microcontroller 114 for controlling and managing the mCAPD process, an input interface 116 for receiving user inputs and providing corresponding commands to the microcontroller 114, and a programmable timer mechanism 118 for controlling the dialysis operation based on user inputs received through the input interface 116. In an embodiment, the programmable timer mechanism 118 includes a real time clock (RTC) chip interfaced to the microcontroller 114 for managing the timing of the dialysis cycles and generating alerts to the user regarding end/start of drain/fill process of a dialysis cycle.

The electronic control board 112 further includes a rechargeable and removable battery 120 for powering the micro-peristaltic pump 103, and the electronic control board 112. In an example, the rechargeable and removable battery 120 can last for more than two days. Further, the microcontroller 114 monitors the battery levels continuously, alerts the user to recharge the exhausted battery and switches to the backup battery when the battery level is low. The electronic control board 112 further includes an LCD display 122 for displaying a dialysis menu, timing parameters of the dialysis cycle, duration of dialysis, status of dialysis, alerts, etc, and a buzzer 124 for alerting the user about the dialysis processes, errors, and/or prompts to connect/empty the fluid bag 102. Further, the input interface 116 includes first, second and third buttons for displaying the dialysis menu on the LCD display 122, and enabling the user to increase/start the dialysis cycle, and decrease/stop the dialysis cycle respectively.

In an embodiment, the fluid flow sensor 110 is an optoelectronic sensor that senses the flow of dialysate fluid flowing through the sterile connector 104, and generates different signals for different hues of color of the dialysate fluid, thus indicating the quality of dialysis after every dialysis cycle. For example, the dark color of the dialysate fluid after the dialysis cycle indicates improper dialysis, and the doctors/patient need to be alerted for taking preventive measures. The microcontroller 114 monitors the dialysis metrics of each dialysis cycle through the fluid flow sensor 110, and automatically logs important data pertaining to the dialysis parameters like quality and quantity of output fluid during fill and drain processes of a dialysis cycle, in a corresponding internal memory. In an embodiment, the microcontroller 114 alerts the user through the buzzer 124 to drain out the fluid bag 102 after the current dialysis cycle, and connect a fresh fluid bag for a successive cycle.

In an embodiment, the microcontroller 114 generates alerts for the patient immediately through the LCD display 120, and/or the buzzer 122, and/or by sending SMS/emails through an mCAPD app running on smartphones, so that instant attention and treatment can be provided, if any abnormal conditions are detected based on the logs. In another embodiment, the data logs stored in the internal memory of the microcontroller 114 may be exported to cloud servers through an android based app, mCAPD running on smartphones for use in patient monitoring system.

In yet another embodiment, the microcontroller 114 be interfaced to a smart phone app through WIFI, Bluetooth, or NFC, for enabling the user to operate the mCAPD system 100 through their smart phone. The smart phone include an intelligent software application, mCAPD, installed therein to serve as a full fledged remote for controlling the mCAPD system 100, by issuing commands for starting/ending fill/drain processes, displaying alerts and dialysis parameters, storing dialysis logs, sending alerts through SMS/emails etc.

Figure 2:
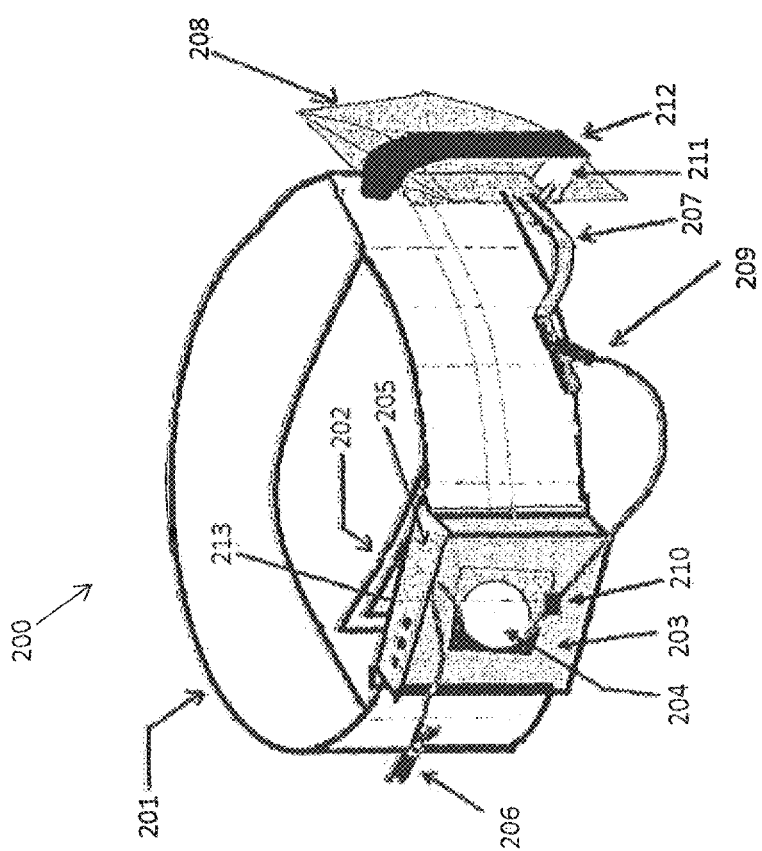
FIG. 2 is a schematic illustration of a wearable mCAPD system in accordance with an embodiment of the present invention.

FIG. 2 is a schematic illustration of a wearable mCAPD system 200, which is an example of the mCAPD system 100, in accordance with an embodiment of the present invention. The wearable mCAPD system 200 includes a wearable belt 201 that can be tied around a waist of a patient, a Velcro pad 202 for tightening the wearable belt 201 around the patient's waist, a mCAPD box 203 mounted on a front portion of the wearable belt 201, a micro-peristaltic pump 204 on a front portion of the mCAPD box 203, a display cum button interface 205 on a top portion of the mCAPD box 203, a first tube 206 attachable to a patient's body, a second tube 207 attachable to a fluid bag 208, a sterile connector 209 connecting the first and second tubes 206 and 207 through the micro-peristaltic pump 204, a fluid flow sensor 210 attached to the sterile connector 209, a load sensor 211 attached to the fluid bag 208, a heating pad 212 attached to the fluid bag 208, a button 213 for opening a top cover of the micro-peristaltic pump 204. In an embodiment, the mCAPD box 203 includes the micro-peristaltic pump 204 and the electronic control board (similar to the electronic control board 112 of FIG. 1) fitted inside therein.

In an embodiment, the micro-peristaltic pump 204 has a button operated top cover. The top cover may be opened and the sterile connector 209 may be placed properly on the guide etched for this purpose in the pump 204, so that the sterile connector 209 comes in partial contact with the circular arms of the pump 204. This arm when rotated in a circular motion, pushes the fluid by simply squeezing the tube 209 on every rotation. This process avoids direct contact of the fluid with any parts of the pump 204, thus removing the risk of infection completely. The corresponding microcontroller controls the start/stop and direction of the fluid flow in accordance to the program, initiated and set by the user.

Upon wearing the wearable mCAPD system 200, a patient can carry on with their dialysis anywhere, even while on the move. In operation, the patient may connect the first tube 206 to their body and turn on the mCAPD box 203, and set the dialysis parameters using the display cum button interface 205, after which the mCAPD box 203 prompts the patient to connect the fluid bag for fill process, and drain bag for the drain process. When the drain process is completed, the wearable mCAPD system 200 may alert the patient, who in turn can dispose the used dialysate fluid in rest rooms. When the patient selects more than one dialysis cycle to be carried out during the day, the audio alerts of the wearable mCAPD system 200 prompt the patient to connect/replace the fluid and drain bags at prescribed intervals. Thus, without affecting any of their lifestyle, the patient can complete the dialysis with minimal inconvenience and disruptions from their daily routine work. The wearable mCAPD system 200 enables the patient to carry out the dialysis anywhere, either from their office, workplace, school or college, without going to a fixed location to carry out the dialysis. The mobility provides a boost to the lifestyle of the patients, and unchains them from their beds, and carry on their lives as normal as possible. This cost effective system can be carried out even by the rural populace who do not have the dialysis facilities in their villages and towns.

The wearable mCAPD system 200 enables the user to carry out day time as well as night time dialysis by using fluid bags of sufficient capacity. For example, during day time dialysis, the patients may have to carry the fluid bags of 1.5 liters, along with them, and connect the fluid bags to the mCAPD box 203 at periodic intervals as alerted by the system. During night dialysis, a 5 liter fluid bag is to be connected to the mCAPD box 203, along with an empty bag of sufficient capacity. Assuming eight hours of sleep by the patient, two cycles of dialysis may be carried out automatically. After completion of two dialysis cycles in the night, the fill process of the third dialysis cycle may be completed by the patient, and after this fill, the patient may be alerted to remove the fluid bag and connect an empty bag to the mCAPD box 203 to collect the drained fluid. Once the drain process of the third cycle is completed, the mCAPD box 203 may alert the patient to discard the drained fluid in a convenient way. Thus, in this way, quota of three dialysis cycles may be completed in total 24 hours.

Figure 3:
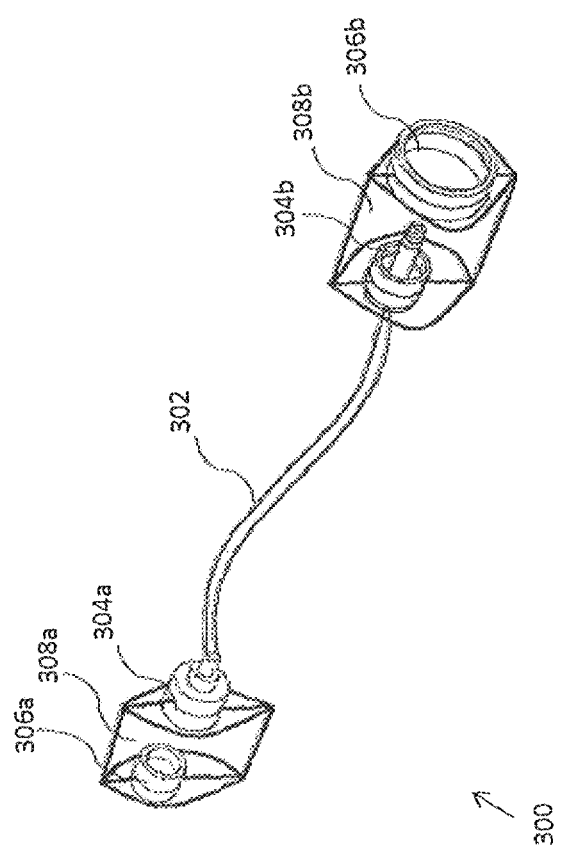
FIG. 3 is a schematic illustration of a sterile connector of FIGS. 1 and 2, in accordance with an embodiment of the present invention.

FIG. 3 is a schematic illustration of a sterile connector 300, which is an example of the sterile connectors 104 and 209, in accordance with an embodiment of the present invention. The sterile connector 300 includes a silicon tube 302 for transferring the dialysate fluid, a first connecting end 304*a* for connecting the silicon tube 302 to a first tube attachable to a peritoneum cavity of the patient's body, a first receiving end 306*a* for receiving the first tube from the patient's body, and a first sterile transparent enclosure 308*a* for providing a sterile environment for connecting the first tube to the first connecting end 304*a*. Similarly, the sterile connector 300 includes a second connecting end 304*b* for connecting the silicon tube 302 to a second tube attachable to a fluid bag, a second receiving end 306*b* for receiving the second tube, and a second sterile transparent enclosure 308*b* for providing a sterile environment for connecting the second tube to the second connecting end 304*b*.

In an example, the first and second sterile transparent enclosures 308*a* and 308*b* are 'Y' shaped plastic casings, that enable the user to connect the silicon tube 302 with the first and second tubes without directly contacting/touching these tubes. The transparent enclosures 308*a* and 308*b* enable connection in a secure, infection free environment, without direct exposure to the unsterile environment. The first and second sterile transparent enclosures 308*a* and 308*b* offer complete protection from infection and avoid the laborious cleansing processes in aseptic environments to carry out the dialysis. The sterile connector 300 is manufactured and packaged in a totally sterile environment, and must be used only once, and to be discarded after a single use.

In operation, a patient may insert the first tube coming from the body into the first receiving end 306*a*, align it with the first connecting end 304*a*, and tighten the first tube with the first connecting end 304*a* through corresponding screw thread arrangement, by holding the corresponding sterile enclosure 308*a*, without physically touching any part of the tubes, thereby eliminating the risk of infection and avoid issues related to infection for the patient. A similar approach may be used to connect the second tube to the silicon tube 302: Thus, without physically opening or touching the tubes, a path is provided for the dialysate fluid to flow into the body from the fluid bag through the first tube inserted into the body through the innovative design of the sterile connector 300.

Figure 4B:
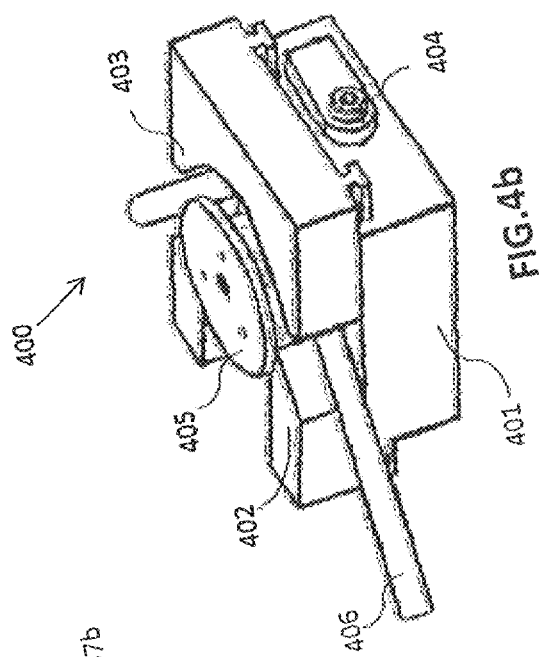
FIGS. 4a and 4b are schematic illustrations of a micro-peristaltic pump in latch closed and open positions respectively, in accordance with an embodiment of the present invention.
Figure 4A:
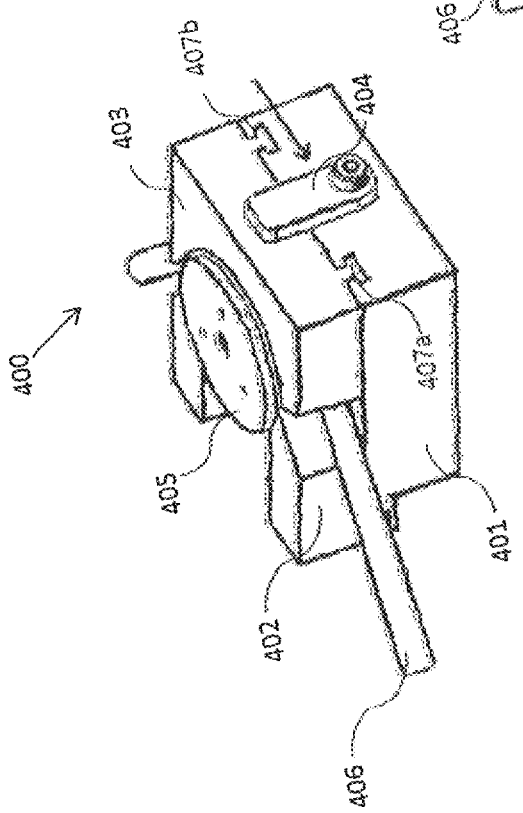

FIGS. 4a and 4b are schematic illustrations of a micro-peristaltic pump 400 in latch closed and open positions respectively, in accordance with an embodiment of the present invention.

The micro-peristaltic pump 400 includes a geared DC motor 401 of sufficient speed and torque uniquely designed for the mCAPD system, a pump base assembly 402 with rotation count mechanism, a movable assembly 403, a latch mechanism 404 to slide and release the movable assembly 403, and a rotor assembly 405.

In an embodiment, the base and movable assemblies 402 and 403 can be glided with respect to each other by a simple T-slot mechanism 407a and 407b. Upon easing of the latch 404, assemblies 402 and 403 slides through T-slots 407a and 407b. During an open position of the latch 404, the gap created between the base and movable assemblies 402 and 403 allows placement of the sterile connector 406 in between the assemblies 402 and 403. By sliding in the movable assembly 403 and tightly clipping the latch 404, brings T-slots 407a and 407b in place, the sterile connector 406 may be effectively inserted inside the pump 400 in a simple and easy manner. The rotor assembly 405 then facilitates pumping of the fluid through the pinching of sterile connector snapped tightly therein through Bernoulli principle.

Figure 5:
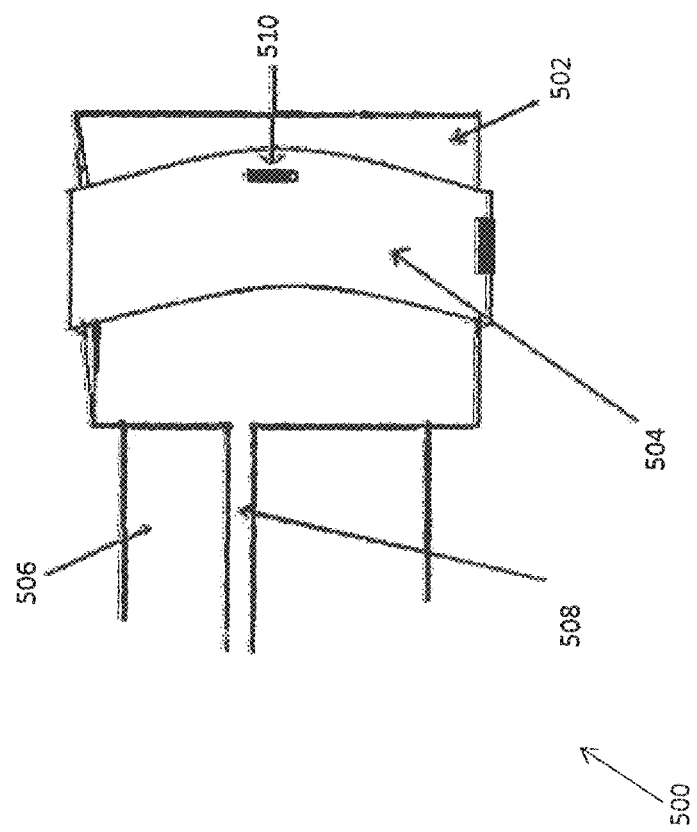
FIG. 5 is a schematic illustration of a heating arrangement for heating the dialysate fluid of the fluid bag, in accordance with an embodiment of the present invention.

FIG. 5 is a schematic illustration of a heating arrangement 500 for heating the dialysate fluid of a fluid bag 502, in accordance with an embodiment of the present disclosure.

The heating arrangement 500 illustrates a heating pad 504 wrapped around the fluid bag 502, a wearable belt 506, a fluid bag tube 508, a temperature sensor 510 for sensing the temperature of the fluid bag 502, and a load cell sensor for sensing the volume of fluid in the fluid bag 502. In an example, the heating pad 504 is fixed along with a strap-on velcro strip, provided to firmly strap the fluid bag 502 to the belt 506. The heating pad 504 may be a specially designed bag with heating element embedded inside therein.

The heating pad 504 facilitates warming of the fluid of the fluid bag 502 before filling it into the cavity to increase the comfort of the patient during the fill process. This option can be set by patient, and automatically be controlled by micro-controller through the temperature sensor 510. The micro-controller powers the heating pad 504 at the required instances before starting the fill process. This avoids a laborious task of heating the fluid separately in conventional CAPD procedure.

In an embodiment of the present invention, another dialysis mechanism Continuous Flow Peritoneal Dialysis (CFPD) can be implemented using the mCAPD system 100. For implementing the CFPD, a small amount of CAPD fluid of up to 100 ml, is taken from the peritoneal cavity by pumping it out through the mCAPD device 100. This fluid is allowed to pass through a sorbent, which filters the toxins like urea, creatinin present in the fluid. The recycled fluid is pumped back into the body through the mCAPD device 100. This process is repeated once in an hour, and a six hour CFPD process is found adequate for maintaining the patient, by adequate removal of urea/creatinin from the blood. This method reduces the cost, fluid overload and its associated disadvantages in the body, and a better all round condition for patients Various embodiments of the present invention provides a system and method for carrying out continuous ambulatory peritoneal dialysis on the move, at any place, outside their hospitals and homes for end stage renal failure patients. The system provides a unique hybrid approach wherein the advantages of a night dialysis and the robustness of day dialysis is offered by implementing two cycles of dialysis during the night, and the fill portion of the third cycle of dialysis. Patients can then move onto their work, routine, and the mCAPD completes the drain process of the third cycle, and alerts the patients to discard the drained fluid at their convenience.

A wearable mobile continuous ambulatory peritoneal dialysis (mCAPD) system, includes an mCAPD module mounted on a front portion of a wearable belt, wherein the mCAPD module comprises a micro-peristaltic pump disposed in a corresponding front portion, and an electronic control board connected to the micro-peristaltic pump for controlling and managing the mCAPD process, a fluid bag containing a dialysate fluid, attached to the wearable belt and to the electronic control board, and a sterile connector having a tube portion fixed into a guide section of the micro-peristaltic pump, and a first connecting end for connecting to a first tube inserted into a peritoneum cavity of the human body, and a second connecting end for connecting to a second tube attached to the fluid bag. Upon rotation, the micro-peristaltic pump enables a flow of fluid between the peritoneum cavity and the fluid bag, through the tube portion of the sterile connector, and a direction and speed of rotation of the micro-peristaltic pump is controlled by the electronic control board.

While the invention has been described in detail, modifications within the spirit and scope of the invention will be readily apparent to those of skill in the art. Such modifications are also to be considered as part of the present invention. In view of the foregoing discussion, relevant knowledge in the art and references or information discussed above in connection with the Background of the Invention, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

I claim:

1. A wearable mobile continuous ambulatory peritoneal dialysis (mCAPD) system, comprising:
   a mCAPD module mounted on a front portion of a wearable belt, wherein the mCAPD module comprises a micro-peristaltic pump disposed in a corresponding front portion, and an electronic control board connected to the micro-peristaltic pump for controlling and managing a mCAPD process;
   a fluid bag containing a dialysate fluid, attached to the wearable belt and to the electronic control board; and
   a sterile connector having:
      a tube portion fixed onto a guide section of the micro-peristaltic pump;
      a first connecting end for connecting to a first tube inserted into a peritoneal cavity of the human body; and a second connecting end for connecting to a second tube attached to the fluid bag, wherein upon rotation, the micro-peristaltic pump enables a flow of fluid between the peritoneum cavity and the fluid bag, through the tube portion of the sterile connector, and wherein a direction and speed of rotation of the micro-peristaltic pump are controlled by the electronic control board, wherein the micro-peristaltic pump comprises:

a static base assembly;

a movable assembly for gliding with respect to the static base assembly through a T-slot mechanism; and a latch configured to release and unlock the movable assembly from the static base assembly, such that during an open position of the latch, the static and movable assemblies slide through one or more T-slots, and a gap created between the static base and movable assemblies allow placement of the sterile connector therebetween.

2. The wearable mCAPD system as claimed in claim 1, further comprising:

a heating element attached to the fluid bag for heating the dialysate fluid; and a fluid flow sensor attached to the sterile connector for measuring a quantity of dialysate fluid flowing therethrough, wherein the electronic control board is connected to the heating element for automatically controlling a temperature of the heating element, and connected to the fluid flow sensor for automatically recording a quantity of the dialysate fluid flowing therethrough.

3. The wearable mCAPD system as claimed in claim 2, wherein the fluid flow sensor is an opto-electronic sensor that generates one or more signals corresponding to one or more hues of color of the dialysate fluid, and wherein the electronic control board automatically analyzes a quality of corresponding dialysis based on the one or more hues of color, and generates one or more alerts in an event of an improper dialysis.

4. The wearable mCAPD system as claimed in claim 1, wherein the electronic control board comprises:

an input interface for receiving one or more user instructions regarding initiation, timings and durations of one or more dialysis cycles;

a programmable timer mechanism for monitoring timings of fill and drain processes of one or more dialysis cycles based on the one or more user instructions, and generating one or more alerts indicating start and end times of one or more fill and drain processes of the one or more dialysis cycles;

a rechargeable battery for powering the micro-peristaltic pump, and the electronic control board;

an LCD display for displaying a dialysis menu, the one or more user instructions, timing parameters of one or more dialysis cycles, status and duration of one or more dialysis cycles, and the one or more alerts; and a buzzer for generating one or more audio alerts at predefined intervals for prompting the user to replace the fluid bag.

5. The wearable mCAPD system as claimed in claim 4, wherein the electronic control board is configured to export one or more records related to dialysis parameters to one or more mobile communication devices.

6. The wearable mCAPD system as claimed in claim 4, wherein the electronic control board is configured to be interfaced with a mobile communication device through at least one of: WIFI, Bluetooth, and NFC, for enabling the user to operate the wearable mCAPD system through the mobile communication device.

7. The wearable mCAPD system as claimed in claim 1, wherein the sterile connector includes:

the tube portion for carrying the dialysate fluid;

first and second receiving ends for receiving the first and second tubes; and the first and second connecting ends for connecting the tube portion to the first and second tubes respectively, wherein the first receiving and connecting ends are enclosed in a first sterile transparent enclosure, and the second receiving and connecting ends are enclosed in a second sterile transparent enclosure for providing a sterile environment for connecting the first and seconds tubes to the first and second connecting ends respectively.

8. The wearable mCAPD system as claimed in claim 7, wherein the first and second sterile transparent enclosures are 'Y' shaped plastic casings.

9. The wearable mCAPD system as claimed in claim 1, wherein a filtering device is connected to the sterile connector for receiving and filtering a dialysate fluid extracted from the peritoneal cavity, and providing the filtered fluid back to the peritoneal cavity, to implement a Continuous Flow Peritoneal Dialysis (CFPD) process using the wearable mCAPD system.

* * * * *